US012220527B2

(12) United States Patent
Poullain et al.

(10) Patent No.: US 12,220,527 B2
(45) Date of Patent: Feb. 11, 2025

(54) NASAL POWDER DELIVERY DEVICE

(71) Applicant: APTAR FRANCE SAS, Le Neubourg (FR)

(72) Inventors: Franck Poullain, La Haye Malherbe (FR); Anne-Cécile Campot, Terres de Bord (FR); Gwénollé Cabillic, Bosc Guerard Saint Adrien (FR); Jaime Arnett, Fishers, IN (US)

(73) Assignee: APTAR FRANCE SAS, Le Neubourg (FR)

( * ) Notice: Subject to any disclaimer, the term of this patent is extended or adjusted under 35 U.S.C. 154(b) by 613 days.

(21) Appl. No.: 17/625,606

(22) PCT Filed: Jul. 9, 2020

(86) PCT No.: PCT/FR2020/051232
§ 371 (c)(1),
(2) Date: Jan. 7, 2022

(87) PCT Pub. No.: WO2021/005311
PCT Pub. Date: Jan. 14, 2021

(65) Prior Publication Data
US 2022/0257884 A1    Aug. 18, 2022

(30) Foreign Application Priority Data

Jul. 10, 2019  (FR) ...................................... 1907756

(51) Int. Cl.
*A61M 15/08*    (2006.01)
*A61M 15/00*    (2006.01)
(52) U.S. Cl.
CPC ........ *A61M 15/08* (2013.01); *A61M 15/0031* (2014.02); *A61M 2202/064* (2013.01); *A61M 2205/073* (2013.01)

(58) Field of Classification Search
CPC .. A61M 15/00; A61M 15/08; A61M 15/0031; A61M 15/085; A61M 2202/064;
(Continued)

(56) References Cited

U.S. PATENT DOCUMENTS 5,810,004 A * 9/1998 Ohki ................. A61M 15/0028
128/203.15
6,055,980 A * 5/2000 Mecikalski ....... A61M 15/0048
128/203.15
(Continued)

FOREIGN PATENT DOCUMENTS

WO    WO-2016090152 A1 *  6/2016   .......... A61M 11/008
WO       2017/191400 A1    11/2017

OTHER PUBLICATIONS

International Preliminary Report on Patentability dated Jan. 11, 2022 with a Translation of the Written Opinion of the International Searching Authority in Application No. PCT/FR2020/051232.
(Continued)

*Primary Examiner* — Timothy A Stanis
*Assistant Examiner* — Tyler A Raubenstraw
(74) *Attorney, Agent, or Firm* — Sughrue Mion, PLLC

(57) ABSTRACT

A nasal powder delivery device having a container containing a dose of powder, a nasal delivery head, and an air discharge system generating a flow of compressed air for delivering a dose of powder into the nostril. An air chamber is arranged in a skirt, and a piston sealingly slides in the air chamber to compress the air. The piston is connected to an actuating member, in which, before actuation, at least one breakable bridge is provided between the skirt and the actuating member, wherein each breakable bridge is formed on the skirt and cooperates with a radial projection formed on the actuating member. Each radial projection has an axial
(Continued)

Figure 1:
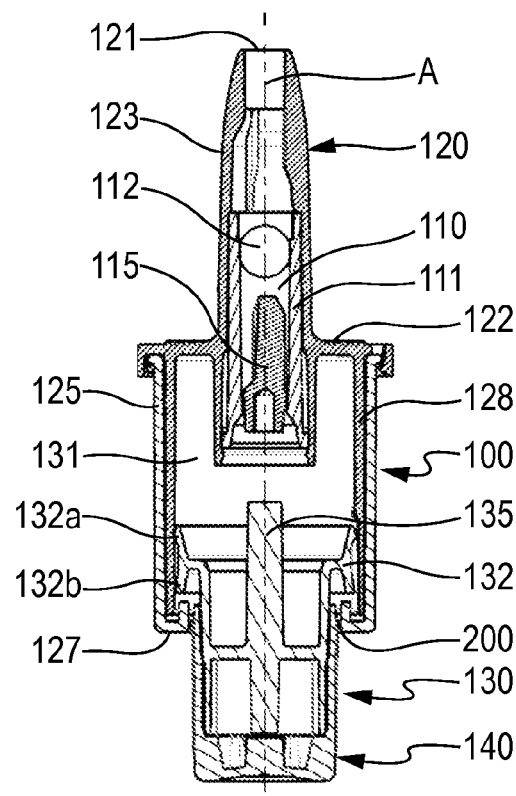

extension greater than that of the respective breakable bridge and forms an inclined axial ramp on either side.

5 Claims, 2 Drawing Sheets

(58) Field of Classification Search
CPC ............ A61M 2205/073; B05B 11/00; B05B 11/0008; B05B 11/0037; B65D 2401/35; B65D 2401/40
USPC .................................................... 222/153.05
See application file for complete search history.

(56) References Cited

U.S. PATENT DOCUMENTS

| | | | |
|---|---|---|---|
| 6,240,918 B1* | 6/2001 | Ambrosio | G06M 1/163 |
| | | | 128/203.15 |
| 6,257,457 B1* | 7/2001 | Oechsel | B05B 11/02 |
| | | | 222/320 |
| 6,321,942 B1* | 11/2001 | Krampen | B05B 15/652 |
| | | | 222/320 |
| 6,708,846 B1 | 3/2004 | Fuchs et al. | |
| 8,684,615 B2* | 4/2014 | Lecoutre | A45D 40/267 |
| | | | 401/122 |
| 8,944,292 B2* | 2/2015 | Moreau | B05B 11/1049 |
| | | | 222/321.9 |
| 9,096,353 B2* | 8/2015 | Pierre | B65D 75/5877 |
| 2012/0103332 A1* | 5/2012 | Parsons | A61M 15/0028 |
| | | | 128/203.15 |
| 2014/0263457 A1* | 9/2014 | Barber | B05B 11/1049 |
| | | | 222/153.13 |
| 2015/0141929 A1* | 5/2015 | Fabien | A61M 5/3287 |
| | | | 604/198 |
| 2015/0290405 A1* | 10/2015 | Papet | A61M 15/009 |
| | | | 128/203.12 |
| 2015/0320943 A1* | 11/2015 | Barber | A61M 11/00 |
| | | | 222/153.13 |
| 2016/0167071 A1* | 6/2016 | Baillet | B05B 11/06 |
| | | | 222/23 |
| 2016/0296957 A1* | 10/2016 | Baillet | B05B 11/0029 |
| 2016/0339464 A1* | 11/2016 | Le Maner | B05B 11/1077 |
| 2019/0126302 A1* | 5/2019 | Decock | B05B 15/30 |

OTHER PUBLICATIONS

International Search Report of PCT/FR2020/051232 dated Nov. 18, 2020 [PCT/ISA/210].

* cited by examiner

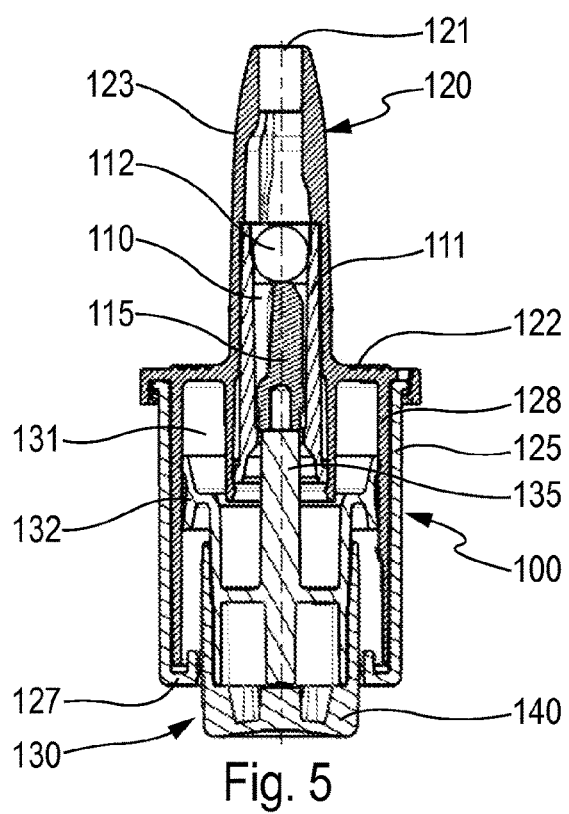
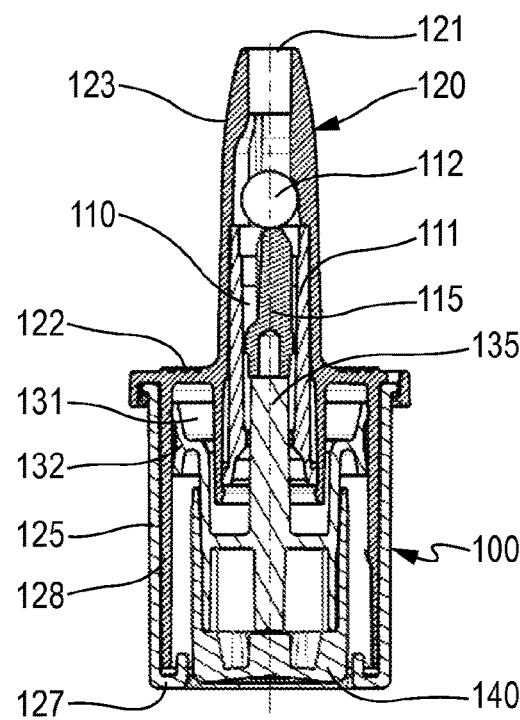
Fig. 5
Fig. 6
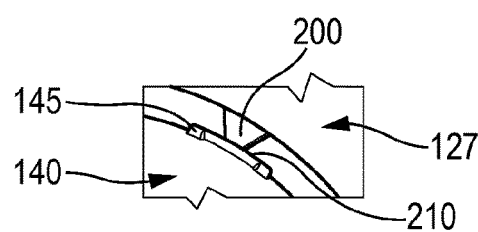
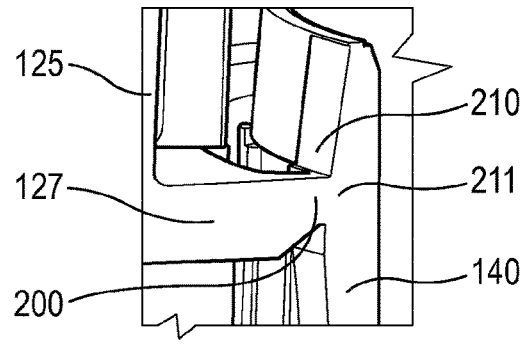
Fig. 7
Fig. 8
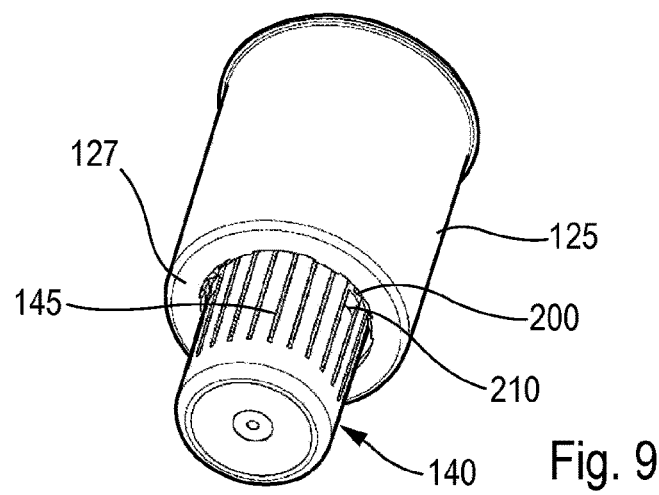
Fig. 9

NASAL POWDER DELIVERY DEVICE

CROSS REFERENCE TO RELATED APPLICATIONS

This application is a National Stage of International Application No. PCT/FR2020/051232 filed on Jul. 9, 2020, claiming priority based on French Patent Application No. 1907756 filed on Jul. 10, 2019.

The present invention relates to a nasal powder delivery device.

Nasal powder delivery devices are well-known. They generally comprise a container containing one or more doses of powder, delivery means, and a nasal delivery head intended to be inserted in a nostril of a user, said nasal delivery head comprising a delivery aperture. The delivery means generally comprise an air discharge system. When the delivery device is actuated, a dose of powder is delivered into a nostril of the user.

A disadvantage of these devices of the prior art relates to the reliability of the device, in particular upon actuation. Thus, generally breakable bridges are provided between two mobile portions against one another upon actuation, in particular to accumulate energy in the hand of the user and to define, in a predetermined manner, the force threshold necessary to achieve the actuation. These breakable bridges however have the disadvantage of sometimes leaving breakable bridge residue or remnants, which can impede, upon actuation of the device.

Documents WO9946055, WO0245866, WO2015001281, WO2017118827, US2016296957, WO2017191400, U.S. Pat. Nos. 6,708,846 and 6,321,942 describe the devices of the state of the art.

The present invention aims to provide a nasal powder delivery device which does not reproduce the abovementioned disadvantages.

The present invention also aims to provide a nasal powder delivery device for a powder which improves the reliability of the device during actuation.

The present invention also aims to provide a nasal powder delivery device which is simple and inexpensive to manufacture and to assemble.

The present invention also aims for a nasal powder delivery device comprising a container containing at least one dose of powder, a nasal delivery head intended to be inserted in a nostril of a user, said nasal delivery head comprising a delivery aperture, and an air discharge system generating, upon actuation of said nasal delivery device for a powder, a flow of compressed air to deliver a dose of powder in said nostril through said delivery aperture, said air discharge system comprising an air chamber, arranged in a skirt, and a piston which upon actuation of the device, sealingly slides in said air chamber to compress the air contained in said air chamber, said piston being rigidly connected to an actuating member, in which, before actuation, at least one breakable bridge is provided between said skirt and said actuating member, each breakable bridge being formed on said skirt and cooperating with a radial projection formed on said actuating member, each radial projection comprising an axial extension greater than that of the respective breakable bridge and forming an inclined axial ramp on either side of the respective breakable bridge.

Advantageously, said skirt comprises, in the vicinity of its axial lower edge, a lower flange, which radially projects inwards, said at least one breakable bridge being formed on a radially inner edge of said lower flange.

Advantageously, the quantity of material of each breakable bridge is minimum at the top of the respective radial projection.

Advantageously, said actuating member comprises, on its outer side surface profiles which radially project outwards, such as longitudinal ridges, each radial projection extending radially outwards at least as much as said projecting profiles.

Advantageously, said container contains one single dose of powder, distributed upon one single actuation of said nasal powder delivery device.

Figure 2:
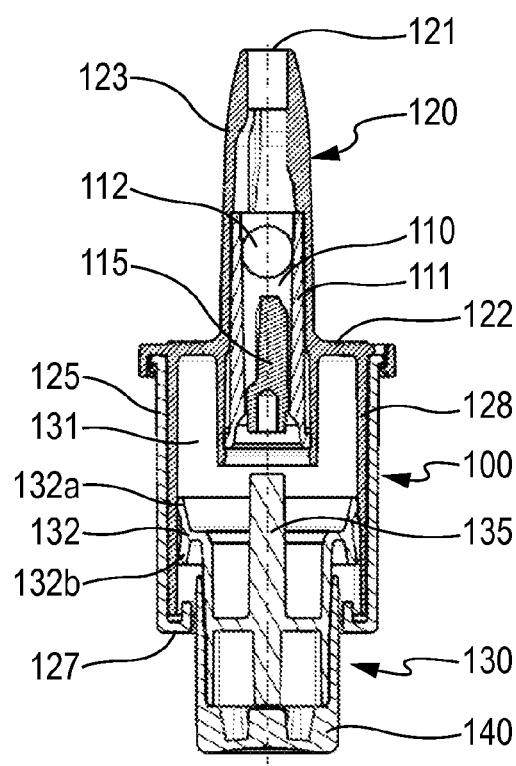
Figure 3:
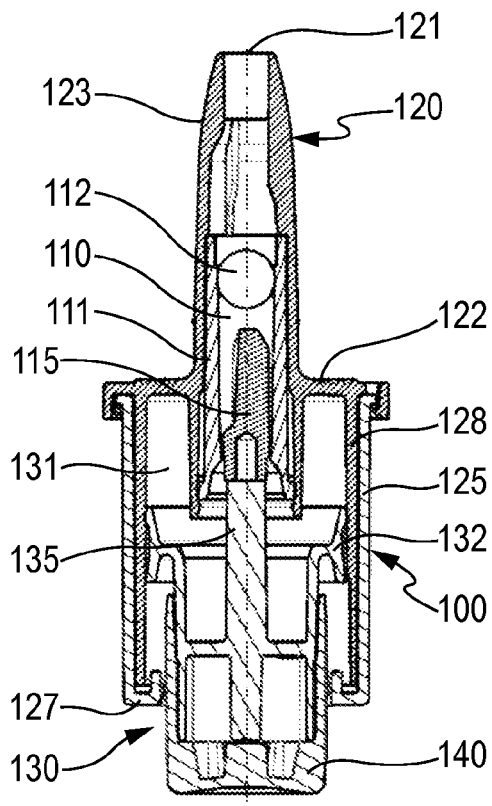
Figure 4:
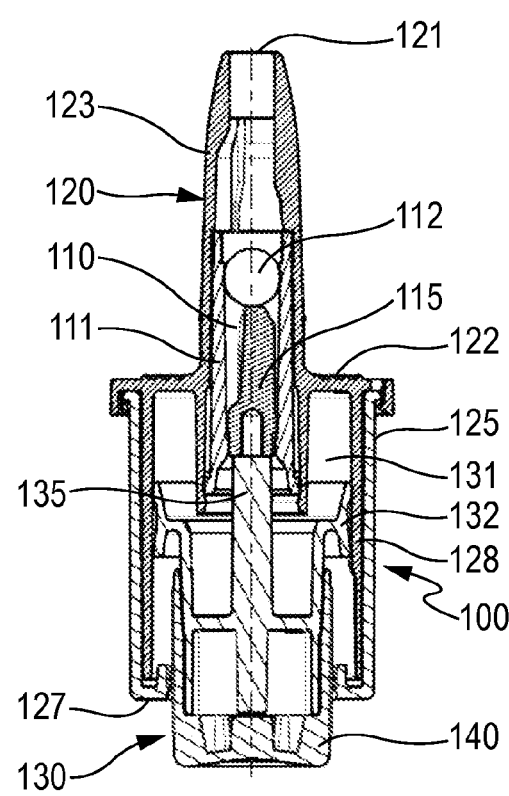

These characteristics and advantages and others will appear more clearly in the following detailed description, made in reference to the appended drawings, given as non-limiting examples, and in which:

FIG. 1 is a schematic cross-sectional view of a nasal powder delivery device according to one advantageous embodiment, in rest position, before actuation, FIG. 2 is a view similar to that of FIG. 1, at the start of actuation, FIGS. 3 to 5 are views similar to that of FIG. 1, showing different positions during actuation, FIG. 6 is a view similar to that of FIG. 1, at the end of actuation, FIGS. 7 and 8 are detailed views, respectively top and side views, of a breakable bridge according to one advantageous embodiment, and FIG. 9 is a schematic, partial perspective view of the two portions of the device connected by breakable bridges before actuation.

In the description, the terms "axial" and "radial" refer to the longitudinal axis A of the device represented in FIG. 1. The terms "proximal" and "distal" refer to the delivery aperture of said device. The terms "top", "bottom", "upper" and "lower" refer to the right position of the device represented in the drawings.

The invention applies more specifically to devices of the single dose of powder type, such as that represented in the figures. Of course, other types of nasal powder delivery devices can also be considered.

The device 100 represented in the figures comprises a container 110 containing one single dose of powder. Devices with a container containing more than one dose are possible. Likewise, devices comprising several containers each containing one single dose are also possible.

A nasal delivery head 120 is assembled on said container 110, said head being intended to be inserted in a nostril of a user. Said nasal delivery head comprises a delivery aperture 121. The delivery head 120 advantageously comprises a finger rest 122 extending radially to facilitate the actuation. A hollow sleeve 123 extends axially upwards from said finger rest 122 and ends at said delivery aperture 121. Preferably, this hollow sleeve 123 is of reduced radial dimension to be able to be inserted in a nostril at the time of the actuation. On the opposite side of the finger rest 122, a skirt 125 extends axially downwards from said finger rest 122. Said skirt 125 comprises, in the vicinity of its axially lower end, a lower flange 127, which radially projects inwards.

The device 100 further comprises an air discharge system 130 generating, upon actuation of said device 100, a flow of compressed air to deliver a dose of powder in said nostril through said delivery aperture 121. Said air discharge system comprises an air chamber 131 and a piston 132 sealingly sliding in said air chamber 131 to compress the air contained in said air chamber 131 and thus generate said flow of compressed air. The piston 132 preferably comprises an upper lip 132a and a lower lip 132b. The air chamber 131 is formed by a hollow axial cylinder 128 which is rigidly connected, preferably at one piece, with the finger rest 122 of the delivery head 120. The lower side of said hollow cylinder 128 is open and blocked by said piston 132. The skirt 125 is thus advantageously arranged around said hollow cylinder 128, and can in particular be formed by a fixed hollow sleeve, for example snap-fitted, in the finger rest 122 of the delivery head 120. The air chamber 131 is advantageously open to the atmosphere before actuation.

The piston 132 is preferably rigidly connected to an actuation member 140 which the user will press upon the actuation to move the piston 132 in the air chamber 131. This actuating member 140 can possibly comprised on its outer side surface of the projecting profiles, such as longitudinal ridges 145, which can be seen in FIG. 9.

Before actuation, at least one breakable bridge 200 is provided between the skirt 125 and the actuating member 140. Advantageously, each breakable bridge 200 is formed on the radially inner edge of the radial flange 127 of the skirt 125 and extends to the actuating member 140. The breaking point, generally defined by a reduced quantity of material, is formed at the contact with the actuating member 140. These breakable bridges 200 allow to prevent an accidental or undesired actuation, during storage or transport, or during an accidental fall. They require the application of a predetermined force to be broken, which allows to generate a certain precompression in the hand of the user. It can have any number of breakable bridges there, for example three distributed around the periphery of the device.

In the example represented in the figures, the container 110 is formed by a hollow tube 111 open at its two axial ends, and closed at its proximal end by a closing element 112, such as a ball, and closed at its distal end by an insert 115. This insert 115 comprises an axial extension forming a rod, and can, upon actuation, slide in said hollow tube 111 to push said closing element 112 outside of its closing position. In this example, the piston 132 of the air discharge system 130 is rigidly connected to an axial projection 135 which extends in the proximal direction, and which, during actuation, will move together with the piston 132 during the compression of the air contained in the air chamber 131. When said projection 135 of the piston 132 comes into contact with said insert 115 of the container 110, a continuation of the movement of the piston 132 will cause the sliding of said insert 115 in said hollow tube 111 outside of its closing position. Said insert 115 will, on the one hand, open the passage between the air discharge system 130 and the container 110 and, on the other hand, cause the expulsion of the closing element 112. Thus, the air compressed in the air chamber 131 will flow into said container and drive the dose of powder outside of said container in the direction of said delivery aperture 121. Documents WO9946055, WO0245866, WO2015001281 and WO2017118827 describe devices of this type. Of course, other types of devices are also possible.

According to the invention, each breakable bridge 200 cooperates with a radial projection 210 formed on the actuating member.

Each radial projection 210 comprises an axial extension greater than that of the breakable bridge and forms an inclined axial ramp on either side of the breakable bridge 200, which can be seen in FIG. 8.

The quantity of material of the breakable bridge 200 is preferably at the most projecting portion or top 211 of the radial projection 210, to guarantee that the breakable bridge will break in this place.

The invention allows to avoid any risk of friction of the breakable bridge once broken, during the actuation stroke. Indeed, as soon as the breakable bridge 200 is broken, at the very start of actuation, the actuating member 140 moves axially with respect to the skirt 125, such that the breakable bridge 200 is offset with respect to the top 211 of the radial projection 210, and therefore away from the outer surface of the actuating member 140. Thus, the risks are eliminated that the breakable bridge rubs against this outer surface upon actuation.

This risk is all the more significant when the outer surface of the actuating member 140 comprises ridges 145. Indeed, in this case, if the actuating member slightly rotates after breaking of the breakable bridges, these can be found facing a ridge, and therefore causing potentially impeding friction. The present invention provides that the radial projections 210 extend radially at least as much as said ridges 145, to limit, even eliminate this risk.

The present invention has been described in reference to one advantageous embodiment, but it is understood that a person skilled in the art can apply any modification to it, without moving away from the scope of the present invention such as defined by the appended claims.

The invention claimed is:

1. A nasal powder delivery device (100) comprising a container (110) containing at least one dose of powder, a nasal delivery head (120) intended to be inserted in a nostril of a user, said nasal delivery head comprising a delivery aperture (121), and an air discharge system (130) generating, upon the actuation of said nasal powder delivery device (100), a flow of compressed air to deliver a dose of powder in said nostril through said delivery aperture (121), said air discharge system comprising an air chamber (131), arranged in a skirt (125), and a piston (132) which, upon actuation of the device, sealingly slides in said air chamber (131) to compress the air contained in said air chamber (131), said piston (132) being rigidly connected to an actuating member (140), characterised in that before actuation, at least one breakable bridge (200) is provided between said skirt (125) and said actuating member (140), each breakable bridge (200) being formed on said skirt (125) and cooperating with a radial projection (210) formed on said actuating member (140), each radial projection (210) comprising an axial extension greater than that of the respective breakable bridge (200) and forming an inclined axial ramp on either side of the respective breakable bridge (200).

2. The device according to claim 1, in which said skirt (125) comprises, in the vicinity of its axially lower edge, a lower flange (127), which radially projects inwards, said at least one breakable bridge (200) being formed on a radially inner edge of said lower flange (127).

3. The device according to claim 1, in which the quantity of material of each breakable bridge (200) is minimum at the top (211) of the respective radial projection (210).

4. The device according to claim 1, in which said actuating member (140) comprises on its outer side surface profiles which radially project outwards, such as longitudinal ridges (145), each radial projection (210) extending radially outwards at least as much as said projecting profiles (145).

5. The device according to claim 1, in which said container (110) contains one single dose of powder, distributed during one single actuation of said nasal powder delivery device (100).

* * * * *